United States Patent
Kwan

[19]

[11] Patent Number: 6,135,769
[45] Date of Patent: Oct. 24, 2000

[54] INTRAOSSEOUS INJECTION SYSTEM

[76] Inventor: Danny Pak-Nam Kwan, 6062 Littlefield Dr., Huntington Beach, Calif. 92648

[21] Appl. No.: 09/197,061

[22] Filed: Nov. 20, 1998

[51] Int. Cl.[7] .............................. A61C 17/02; A61C 3/02
[52] U.S. Cl. ............................. 433/80; 433/165; 606/80; 604/164
[58] Field of Search ................................. 433/80, 89, 165, 433/134; 606/80, 167, 172, 181, 185; 604/158, 188, 164, 161, 165, 166

[56] References Cited

U.S. PATENT DOCUMENTS

| | | | |
|---|---|---|---|
| 4,021,920 | 5/1977 | Kirschner et al. | 433/165 X |
| 4,787,893 | 11/1988 | Villette | 604/188 |
| 4,944,677 | 7/1990 | Alexandre | 433/165 |
| 5,057,013 | 10/1991 | Dillon | 433/165 |
| 5,173,050 | 12/1992 | Dillon | 433/165 |
| 5,429,504 | 7/1995 | Peltier et al. | 433/165 |
| 5,569,035 | 10/1996 | Balfour et al. | 433/165 |
| 5,779,708 | 7/1998 | Wu | 606/80 |

*Primary Examiner*—Nicholas D. Lucchesi
*Attorney, Agent, or Firm*—Knobbe, Martens, Olson & Bear LLP

[57] ABSTRACT

An apparatus for intraosseous injection for dental application comprising a hollow drill (1) having a perforation or perforations (2) along its length and a beveled cutting end (3), fitted into a hub (4) of partly circular and partly hexagonal external cross-section and provided with a circumferential lip (5) and a funnel-shaped orifice (6) giving access to the open end of the said hollow drill at its end remote from the said cutting end, and an adapter (7) removably mated with the said hub by means of a matching orifice of substantially hexagonal cross-section and having at its end remote from said orifice a shank (8) shaped to fit into the chuck of a standard contra-angle dental handpiece, and a protective cap (9) fitted over the said hollow drill. After piercing the cortical bone with the hollow drill, the adapter and handpiece are removed leaving an unobstructed passage through the hollow drill to the cancellous bone for the insertion of a conventional dental needle for the injection of anesthetic or other solution to the cancellous bone via the perforations, 2, after which the hollow drill is withdrawn and disposed of.

6 Claims, 1 Drawing Sheet section I-I section II-II section III-III section IV-IV

INTRAOSSEOUS INJECTION SYSTEM

BACKGROUND

1. Field of Invention

This invention relates to a simplified method of intraosseous injection for dental and other applications.

2. Background and Description of Prior Art

The benefits of intraosseous injection for dental work are well known and documented. The method consists of introducing anesthetic solution to the cancerous bone surrounding the roots of the tooth or teeth to be treated. This requires first penetrating the hard but relatively thin cortical mandibular or maxillary bone, after applying a local anesthetic to the gingival tissue of the patient's gum. Previous inventions pose serious problems in application of the method for dental practitioners, or are technically complex and expensive. For example in U.S. Pat. No 4,787,893 to Villette (1988) an extremely complicated and expensive apparatus is described. It comprises a special piece of equipment which drills a hypodermal needle into the cancellous bone and then allows anesthetic solution to be introduced through the same needle.

Apart from the expense of the apparatus there is the attendant problem of the hollow point of the hypodermal needle becoming clogged with bone fragments, thus precluding the injection of anesthetic solution. This problem has been addressed in various other inventions. For example in U.S. Pat. No. 4,944,677 to Alexandre (1990), U.S. Pat. No. 5,057,013 to Dillon et al (1991), and U.S. Pat. No. 5,173,050 also to Dillon (1992), a solid drill is used to perforate the cortical bone then withdrawn to permit the insertion of a conventional hypodermal needle to deliver the anesthetic solution. Devices of this type are in common use, but have the serious disadvantage that having withdrawn the drill the dental practitioner frequently has difficulty in locating the hole in the bone through which to insert the hypodermal needle, particularly when the gingival tissue is displaced laterally during the initial drilling. In U.S. Pat. No 5,779,708 to Cyberdent Inc. (1998) this problem is addressed by using a hollow drill, the hollow bore of which is filled by a removable stylet during drilling so as to prevent blocking with bone fragments. The stylet is subsequently removed allowing a hypodermal needle to be introduced through the hollow drill which is left in place in the patient's jaw bone for the injection of anesthetic solution. This application describes an invention which achieves the same object but in an even simpler and cheaper way.

OBJECTS AND ADVANTAGES

The objects and advantages of the present invention are
a) to provide a means of introducing anesthetic solution to the cancellous bone for dental purposes;
b) to meet object a) in a simple, cheap and effective way;
c) to meet object a) by a means which affords the dental practitioner with ease and convenience of application;
d) to meet object a) while at the same time eliminating the risk of transmission of disease;
e) to meet object a) in such a way as to cause the minimum discomfort to the patient.
f) to meet the above objects in a neat and simple manner in a device which is inexpensive to manufacture;
g) to meet the above objects in a manner which will impose no significant safety hazard to either dental practitioner or patient.

Advantages of the invention are that it reduces the number of steps in the procedure of intraosseous anesthetic injection to a minimum consistent with the removal of the need to purchase expensive equipment. The method of operation means the dental practitioner can effect the introduction of anesthetic solution quickly, thereby saving costs, and always effectively by removing the need to search for the hole in the cortical bone. The present invention allows the use of only one dental needle for the injection of anesthetic solution both intraosseously and locally, rather than the two required by some existing commercial systems.

DRAWING FIGURES

One drawing, sheet 1, accompanies the application.

Figure 1:
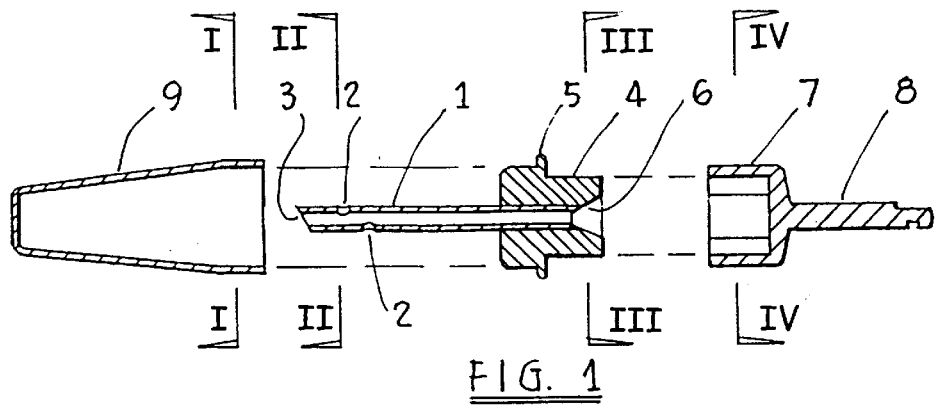
FIG. 1 shows a longitudinal sectional view of the parts of the apparatus.
Figure 1A:
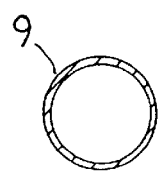
FIGS. 1A, 1B, 1C and 1D show the cross-sectional shapes of the parts of the apparatus.

REFERENCE NUMERALS IN DRAWINGS 1 hollow drill
2 perforations
3 beveled cutting end
4 hub
5 circumferential lip
6 funnel shaped orifice
7 adapter
8 adapter shank
9 protective cap

SUMMARY

In accordance with the present invention a means of injecting anesthetic solution through the cortical bone to the cancellous bone for dental purposes using by way of an adapter in a conventional contra-angle dental handpiece a bevel-tipped hollow drill having a perforation or perforations along its length which is detachable from the adapter after drilling, thereby remaining temporarily in the patient's jaw so as to provide a pathway for a conventional dental needle to deliver the anesthetic solution.

DESCRIPTION FIG. 1

Figure 1B:
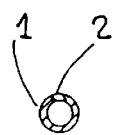
Figure 1C:
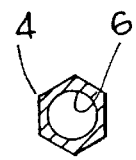
Figure 1D:
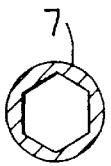
Figure 1E:
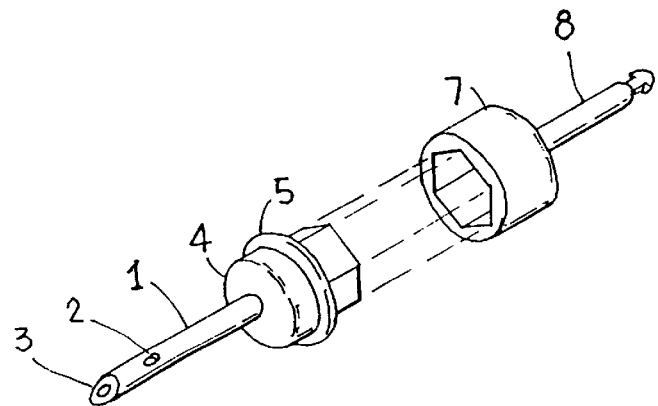
FIG. 1E shows an isometric view of the parts of the apparatus.

A typical embodiment of the present invention is shown in FIG. 1. A hollow drill, 1, having a beveled cutting end, 3, and one or more perforations, 2, along its length is mounted in a hub, 4, having at its end remote from the cutting end of the drill a funnel shaped orifice, 6, connecting with the rear open end of the drill, 1. The hub, 4, incorporates a circumferential lip, 5, facilitating the separation of the hub, 4, from the adapter, 7, on completion of drilling, and removal of the drill from the patient's jaw on completion of the operation. The hub, 4, and the adapter, 7, are mated by way of a hexagonal cross-section as shown in FIGS. 1C and 1D, enabling the adapter, 7, to transmit rotational movement from a standard contra-angle dental handpiece to the drill, 1. The shank, 8, of the adapter, 7, is shaped to fit the chuck of a standard contra-angle dental handpiece. As supplied, the drill, 1, is protected by a removable cap, 9, and the whole assembly is supplied in a sterile condition in a disposable wrapper.

OPERATION FIG. 1

The manner of operation of the present invention is simple. The dental practitioner selects the site where he wishes to pierce the patient's cortical bone and applies a local anesthetic into the gingival tissue with a conventional dental syringe. The shank of the apparatus, 7, is fitted into the chuck of a standard contra-angle dental handpiece and the protective cap, 9, removed. The drill is then applied at the selected anesthetized site until the cortical bone is penetrated. By restraining the drill using the lip, 5, the said handpiece and adapter, 7, are then removed. Using a conventional dental syringe, which may be the same one as used for the foregoing local anesthesia, the dental needle is inserted into the drill, 1, facilitated by the funnel shaped orifice, 6, and the required quantity of anesthetic solution slowly injected into the cancerous bone. The dental needle is then withdrawn following which the drill, 1, is also removed and safely disposed of, together with the adapter, 7, and the conventional dental needle.

CONCLUSION, RAMIFICATIONS AND SCOPE

Accordingly the reader will see that the intraosseous drill of this invention can be used to safely facilitate the introduction of anesthetic solution to a patient's jaw for dental purposes. Its operation is simple and reliable. By placing the perforations, 2, in the wall of the drill, 1, as shown in FIG. 1B, the risk of blocking the path of the anesthetic solution with bone fragments during drilling is eliminated even if the beveled cutting end of the drill is blocked, and by using the hollow drill as a guide for the subsequent insertion of a conventional dental needle, the risk of the dental practitioner experiencing difficulty in finding, or even being unable to find the hole in the cortical bone, as happens in other systems, is also eliminated. Furthermore the present invention has the advantages that a) it is cheap to manufacture compared with other complex systems b) it requires the use of a standard contra-angle dental handpiece which virtually every dental practitioner already has available c) because the whole assembly is so short, access to difficult parts of the patient's mouth is facilitated and the patient's discomfort reduced to a minimum d) it requires no special techniques or particular training for the dental practitioner to be able to use it effectively e) by being completely disposable it obviates the risk of spreading infectious diseases.

Although the foregoing description contains many specificities, these should not be construed as limiting the scope of the invention but as merely providing illustrations of some of the currently preferred embodiments of the invention. For example, the mating surfaces of the hub, 4, and the adapter, 7, may be of many shapes other than hexagonal, from square to splined. The material from which both the hub, 4, and the adapter, 7, are made may be plastics or metal. The beveled cutting end of the drill may be closed.

The configuration of the perforations, 2, may be such that their direction relative to the cross-section of the drill, 1, is from radial to almost tangential, and their shape may be circular or elliptical or any other suitable shape.

Thus the scope of the invention should be determined by the appended claims and their legal equivalents, rather than by the examples given.

I claim:

1. An apparatus for performing intraosseous injections, comprising.

a hollow drill, said drill defined by at least one perforation along its length, a beveled cutting end, and a hub end, further including a hub attached to said drill at said hub end, said hub formed of plastic and further having first end adjacent to said drill, said first end having a cylindrical external cross section, and further defining a second end having a hexagonal external cross-section;

said hub further having a raised circumferential lip, and a funnel-shaped orifice for connecting said hub with said hub end whereby said hub removably mates with said drill by cooperation of an adapter, said adapter having at hexagonal end for mating with said hexagonal cross section and a shank end for mating with a dental handpiece.

2. The apparatus of claim 1, wherein the beveled cutting end of said drill is closed.

3. The apparatus of claim 1, wherein the mating sections of said hub and said adapter are.

4. The apparatus of claim 1, wherein said hub is made of non-plastic material.

5. The apparatus of claim 1, wherein the mating sections of said hub and said adapter are splined.

6. The apparatus of claim 1, wherein said adapter is made of non-plastic material.

* * * * *